(12) United States Patent
Bortolin et al.

(10) Patent No.: US 7,879,543 B2
(45) Date of Patent: Feb. 1, 2011

(54) METHOD OF DETECTING MUTATIONS ASSOCIATED WITH THROMBOSIS

(75) Inventors: Susan Bortolin, Oakville (CA); Frank Merante, Etobicoke (CA); Daniel Kobler, Toronto (CA); Daniel Fieldhouse, Bolton (CA); Margot Boszko, Toronto (CA); Hemanshu Modi, Brampton (CA); Richard A. Janeczko, Oakville (CA); Roman Zastawny, Etobicoke (CA)

(73) Assignee: Luminex Molecular Diagnostics, Inc., Toronto (CA)

( * ) Notice: Subject to any disclaimer, the term of this patent is extended or adjusted under 35 U.S.C. 154(b) by 896 days.

(21) Appl. No.: 10/579,584

(22) PCT Filed: Nov. 17, 2004

(86) PCT No.: PCT/CA2004/001974

§ 371 (c)(1),
(2), (4) Date: Mar. 12, 2007

(87) PCT Pub. No.: WO2005/047533

PCT Pub. Date: May 26, 2005

(65) Prior Publication Data

US 2007/0160992 A1 Jul. 12, 2007

Related U.S. Application Data

(60) Provisional application No. 60/520,303, filed on Nov. 17, 2003.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.33
(58) Field of Classification Search ................ 435/91.2; 536/24.33
See application file for complete search history.

(56) References Cited

U.S. PATENT DOCUMENTS 6,812,339 B1 * 11/2004 Venter et al. ............. 536/24.31
7,608,398 B2 * 10/2009 Pancoska et al. ............... 435/6

FOREIGN PATENT DOCUMENTS

| EP | 1398388 A2 | 3/2004 |
|---|---|---|
| GB | 2338062 A | 12/1999 |
| WO | WO 00/11034 A1 | 3/2000 |
| WO | WO 00/47766 A1 | 8/2000 |
| WO | WO-01/29260 A2 | 4/2001 |
| WO | WO-01/71028 A2 | 9/2001 |
| WO | WO 01/71028 A2 * | 9/2001 |
| WO | WO 02/059355 A2 | 8/2002 |
| WO | WO 2004/072887 A2 | 8/2004 |

OTHER PUBLICATIONS

Humeny et al. (2001) Clinical Biochemistry 34 pp. 531-536.*
Dunbar et al., "Factor V Leiden Profile," Excerpt of poster presented at 33rd Annual Oak Ridge Conference, May 4-5, 2001, Seattle, WA (4 pages).
Bortolin, S., et al. (2004) "Analytical Validation of the Tag-It High-Throughput Microsphere-Based Universal Array Genotyping Platform: Application to the Multiplex Detection of a Panel of Thrombophilia-Associated Single-Nucleotide Polymorphisms," Clinical Chemistry, 50(11): 2028-2036.
Mitterer, M., et al. (1999) "Simultaneous Detection of FV Q506 and Prothrombin 20210A Variation by Allele-Specific PCR," Haematalogica (84)3: 204-207.
Ulvik, et al. (1998) "Simultaneous Determination of Methylenetetrahydrofolate Reductase C677T and Factor V G1691A Genotypes by Mutagenically Separated PCR and Multiple-Injection Capillary Electrophoresis," Clinical Chemistry, 44(2): 264-269.
Endler, G. et al., "Multiplexed mutagenically separated PCR: simultaneous single-tube detection of the factor V R506Q (G1691A), the prothrombin G20210A, and the methylenetetrahydrofolate reductase A223V (C677T) variants," (2001) *Clin. Chem.* 47(2): 333-335.
Neitzel, B. et al., "Easy, accurate and reliable screening for SNPs by ion pair/reverse phase HPLC: simultaneous detection of factor V G1691A, prothrombin G20210A and methylenetetrahydrofolate reductase C677T variants," *Clin. Lab.* (2003) 49(7-8): 313-318.
International Search Report for International Application No. PCT/CA2004/001974, completed Mar. 10, 2005 (3 pages).

* cited by examiner

*Primary Examiner*—Suryaprabha Chunduru
(74) *Attorney, Agent, or Firm*—Goodwin Procter LLP

(57) ABSTRACT

The present invention provides a method for the simultaneous identification of two or more single base changes in a plurality of target nucleotide sequences that are markers associated with cardiovascular diseases such as deep vein thrombosis and the like. Multiplex detection is accomplished using multiplexed tagged allele specific primer extension (ASPE) and hybridization of such extended primers to a probe, preferably an addressable anti-tagged support.

11 Claims, 6 Drawing Sheets

METHOD OF DETECTING MUTATIONS ASSOCIATED WITH THROMBOSIS

CROSS REFERENCE TO RELATED APPLICATIONS

This application is the national stage of International (PCT) Patent Application Ser. No. PCT/CA2004/001974, filed Nov. 17, 2004, and published under PCT Article 21(2) in English, which claims the benefit of and priority to U.S. Provisional Patent Application Ser. No. 60/520,303, filed Nov. 17, 2003. The entire disclosure of International Patent Application Ser. No. PCT/CA2004/001974 is incorporated by reference herein for all purposes.

BACKGROUND OF THE INVENTION

1. Field of the Invention

The present invention relates to methods and kits for the detection mutations associated with thrombosis.

2. Description of the Prior Art

Venous thromboembolism (VTE) disease also called venous thrombosis, which manifests clinically as deep vein thrombosis (DVT) and pulmonary embolisms (PE), represents a major health problem worldwide. A DVT is a blood clot that forms in leg veins. A PE is caused by a blood clot, typically in the leg, groin, or pelvic veins (and occasionally in upper extremity veins), which breaks free and travels to the lung arteries. A DVT is often the source of a clot that travels to the lung arteries and becomes a PE.

VTE is a multifactorial disease which is caused not only by multiple genetic factors but also by multiple acquired or environmental risk factors, such as surgery, use of oral contraceptives, hormone replacement therapy, and advanced age. The incidence of symptomatic venous thrombosis cases is approximately 1 in 1000 people per year. Various gene-gene, gene-environment, and environment-environment interactions between risk factors work synergistically to increase the risk of an individual to VTE. Despite recognition of risk factors and availability of pharmacologically effective options for prophylaxis, DVT and PE remain common causes of morbidity and mortality.

Several single nucleotide polymorphisms (SNPs) associated with VTE have been identified. The factor V Leiden polymorphism (G1691A) (Genbank Accession #Z99572) has been identified as the most common inherited cause, and is implicated in 20 to 40% of venous thrombosis cases. Heterozygotes possess a 3 to 7-fold increased risk of thrombosis while homozygous mutants carry a 50 to 100-fold increased risk. The second most common cause of inherited thrombophilia involves the factor II (prothrombin) G20210A polymorphism (Genbank Accession #M17262). This mutation results in elevated levels of factor II through mRNA stabilization and accounts for 6 to 8% of venous thrombosis cases. Factor II heterozygotes carry about a 2 to 5-fold increased risk of venous thromboembolism in the absence of other risk factors and a more than additive synergistic risk when other risk factors, especially oral contraceptive use, are present. Approximately 10 to 12% of factor V heterozygotes with venous thrombosis also carry the factor II mutation. A third independent risk factor for thrombosis, is the methylenetetrahydrofolate reductase (MTHFR)C677T polymorphism (Genbank Accession #NM005957.1). This mutation produces an MTHFR protein with reduced activity resulting in an increased serum level of homocysteine. This polymorphism is extremely common with homozygote frequencies of 5 to 15%. Furthermore, this polymorphism is also a risk factor for atherosclerotic heart disease, pre-eclampsia and fetal neural tube defects. There is a general consensus that the three aforementioned SNPs are the most important mutations associated with thrombophilia. Three additional SNPs, MTHFR A1298C (Genbank Accession #NM005957.1), factor XIII val34leu (factor XIII G4377T Genbank Accession #AF418272) and tissue factor plasma inhibitor (TFPI) C536T (GenBank Accession #M59497), are believed to have little or no independent effect on venous thrombosis. However, they may act synergistically with other genetic or acquired risk factors resulting in a more than additive effect or, in the case of factor XIII val34leu, a protective effect.

Individual polymorphisms, as described above, may have little or no independent effect on venous thrombosis but may act synergistically with other genetic or acquired risk factors, resulting in a more than additive effect. While approaches for providing this information by analyzing one gene at a time are currently available, the ability to detect all of the above mutations simultaneously would be extremely useful in establishing a complete picture of a patient's genetic risk profile.

Methodologies which can be used to detect the above mentioned SNPs are characterized by specific deficiencies. There are currently no rapid methods for determining several mutations across a number of genes simultaneously. For example, DNA sequencing of the above mentioned alleles for a large number of samples would require several days for simplex Polymerase Chain Reaction (PCR) amplification of individual SNPs, amplicon purification, sequencing reaction set-up and electrophoresis. This would have to be repeated for each of the amplicons generated representing the individual SNPs. Analysis of the sequencing data involves additional time.

Multiplex Allele Specific Primer Extension and Solid Support Detection of SNPs

Multiplex allele specific primer extension, and hybridization of extended primers to a solid support is described generally in the prior art. ASPE technology has been generally described in U.S. Pat. No. 4,851,331. The technology is designed to identify the presence or absence of specific polymorphic sites in the genome.

Multiplex ASPE in conjunction with hybridization to a support for mutation detection can be described generally as follows:

1) Amplifying regions of DNA comprising polymorphic loci utilizing a multiplexed, PCR.

2) Allele specific extension of primers wherein the amplified regions of DNA serve as target sequences for the allele specific extension. Extension primers that possess a 3' terminal nucleotide which form a perfect match with the target sequence are extended to form extension products. Modified nucleotides are incorporated into the extension product, such nucleotides effectively labelling the extension products for detection purposes. Alternatively, an extension primer may instead comprise a 3' terminal nucleotide which forms a mismatch with the target sequence. In this instance, primer extension does not occur unless the polymerase used for extension possesses exonuclease activity.

3) Hybridizing the extension product to a probe on a solid support, such as a microarray, wherein the probe is complementary to the 5' end of the extension product.

The extension primers used in a methodology as described above, possess unique sequence tags at their 5' ends. For example, the sequence tags may allow the extension products to be captured on a solid support.

Variations of the above technology have been described, for example, in U.S. Pat. No. 6,287,778 and PCT Application (WO 00/47766).

It is an object of the present invention to provide a method for the detection of variants associated with thrombosis.

SUMMARY OF THE INVENTION

In one aspect, the present invention provides a method for detecting the presence or absence of a variant nucleotide in at least two SNP sites associated with thrombosis, the SNP sites selected from the group consisting of Factor V Leiden G1691A, Prothrombin (Factor II) G20210A, MTHFR677T, MTHFR A1298C, Factor XIII G4377T, and tissue factor plasma inhibitor (TFPI) C536T, the method comprising the steps of;

a) amplifying regions of DNA containing the at least two SNP sites to form amplified DNA products;

b) hybridizing at least two tagged allele specific extension primers to a complementary target sequence in the amplified DNA products, wherein each tagged allele specific extension primer has a 3'-end hybridizing portion substantially complementary to an allele of one of the SNP sites associated with thrombosis and a 5'-end tag portion complementary to one of a set probes, the terminal nucleotide of the 3' end hybridizing portion being either complementary to a suspected variant nucleotide or to the corresponding wild type nucleotide of the SNP site;

c) extending the at least two tagged allele specific extension primers, using labelled nucleotides, if the terminal nucleotide of the 3' end hybridizing portion is a perfect match to an allele of one of the SNP sites in the amplified DNA products;

d) hybridizing the at least two allele two tagged allele specific extension primers to the set of probes and detecting the presence of labelled extension products.

In another aspect, in the method of the present invention the at least two tagged allele specific extension primers have a 3' end hybridizing portion corresponding to bases 25 and up of any two of SEQ ID NO: 1 to SEQ ID NO: 12.

In another aspect, in the method of the present invention the at least two tagged allele specific extension primers have a 5'-end tag portion comprising a sequence corresponding to bases 1 to 24 of any two of SEQ ID NO: 1 to SEQ ID NO: 12.

In another aspect, in the method of the present invention the at least two tagged allele-specific extension primers are selected from the group consisting of SEQ ID NO: 1 to SEQ ID NO: 12.

In another aspect, the present invention provides a kit for use in detecting the presence or absence of a variant nucleotide in at least two SNP sites associated with thrombosis, the SNP sites selected from the group consisting of Factor V Leiden G1691A, Prothrombin (Factor II) G20210A, MTHFR C677T, MTHFR1298C, Factor XIII G4377T, and tissue factor plasma inhibitor (TFPI) C536T, the kit comprising a set of at least two tagged allele specific extension primers wherein each tagged allele specific extension primer has a 3'-end hybridizing portion substantially complementary to a first allele of one of the SNP sites associated with thrombosis and a 5'-end tag portion complementary to one of a set probes.

In another aspect, the present invention provides a kit for use in detecting the presence or absence of a variant nucleotide in at least two SNP sites associated with thrombosis, the SNP sites selected from the group consisting of Factor V Leiden G1691A, Prothrombin (Factor II) G20210A, MTHFR C677T, MTHFR A1298C, Factor XIII G4377T, and tissue factor plasma inhibitor (TFPI) C536T, the kit including at least two tagged allele specific extension primers having a 3' end hybridizing portion corresponding to bases 25 and up of any two of SEQ ID NO: 1 to SEQ ID NO: 12.

In another aspect, the present invention provides a kit for use in detecting the presence or absence of a variant nucleotide in at least two SNP sites associated with thrombosis, the SNP sites selected from the group consisting of Factor V Leiden G1691A, Prothrombin (Factor II) G20210A, MTHFR C677T, MTHFR A1298C, Factor XIII G4377T, and tissue factor plasma inhibitor (TFPI) C536T, the kit including at least two tagged allele specific extension primers selected from the group consisting of SEQ ID NO: 1 to SEQ ID NO: 12.

In another aspect, the present invention provides a kit for use in detecting the presence or absence of a variant nucleotide in at least two SNP sites associated with thrombosis, the SNP sites selected from the group consisting of Factor V Leiden G1691A, Prothrombin (Factor II) G20210A, MTHFR C677T, MTHFR A1298C, Factor XIII G4377T, and tissue factor plasma inhibitor (TFPI) C536T, the kit including at least two tagged allele specific primers having a 5'-end tag portion comprising a sequence corresponding to bases 1 to 24 of any two of SEQ ID NO: 1 to SEQ ID NO: 12.

In another aspect the present invention provides a kit for use in detecting the presence or absence of a variant nucleotide in at least two SNP sites associated with thrombosis, the SNP sites selected from the group consisting of Factor V Leiden G1691A, Prothrombin (Factor II) G20210A, MTHFR C677T, MTHFR A1298C, Factor XIII G4377T, and tissue factor plasma inhibitor (TFPI) C536T, the kit comprising a set of PCR amplification primers for amplifying regions of DNA containing the at least two SNP sites, the set comprising at least two pairs of PCR primers selected from the group of pairs consisting of:

SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, and SEQ ID NO: 23 and SEQ ID NO: 24.

BRIEF DESCRIPTION OF THE DRAWINGS

These and other features of the preferred embodiments of the invention will become more apparent in the following detailed description in which reference is made to the appended drawings wherein.

DESCRIPTION OF THE PREFERRED EMBODIMENTS

Figure 1:
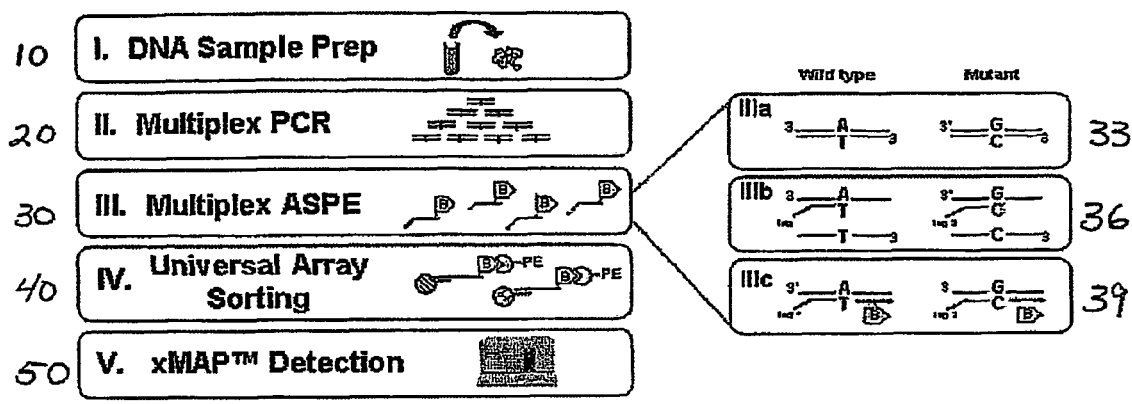
FIG. 1 depicts a general overview of steps of the present invention.

Definitions:

The following terms used in the present application will be understood to have the meanings defined below:

The term single nucleotide polymorphism (SNP), as used herein represents one of the most common forms of genetic variation. These polymorphisms occur when a single nucleotide (A, G, C or T) in the genome is altered. SNPs generally tend to be evolutionarily stable from generation to generation and, as such, can be used to study specific genetic abnormalities throughout a population. SNPs often occur in protein coding regions and, as a result, may lead to the expression of a defective or variant form of a protein. Such polymorphisms can therefore serve as effective indicators of genetic disease. However, not all SNPs are found in protein coding regions of the genome. Some SNPs are located in noncoding regions, but these polymorphisms may also lead to altered protein expression. Specifically, SNP sites in noncoding regions may, for example, lead to differential and defective splicing. In diseases where multiple genes may influence the onset of the disease, SNPs can be used as diagnostic tools for identifying individuals with a predisposition for manifesting the disease, genotyping the patients suffering from the disease in terms of the genetic causes underlying the condition, and facilitating drug development based on the insight revealed regarding the role of target proteins in the pathogenesis process.

The terms "oligonucleotide" and "polynucleotide" as used in the present application refer to DNA sequences being of greater than one nucleotide in length. Such sequences may exist in either single or double-stranded form. Examples of oligonucleotides described herein include PCR primers, ASPE primers, and anti-tags.

The term "allele" is used herein to refer to variants of a nucleotide sequence.

The expression "allele specific primer extension (ASPE)", as used herein, refers to a mutation detection method utilizing primers which hybridize to a corresponding DNA sequence and which are extended depending on the successful hybridization of the 3' terminal nucleotide of such primer. Amplified regions of DNA serve as target sequences for ASPE primers. Extension primers that possess a 3' terminal nucleotide which form a perfect match with the target sequence are extended to form extension products. Modified nucleotides can be incorporated into the extension product, such nucleotides effectively labelling the extension products for detection purposes. Alternatively, an extension primer may instead comprise a 3' terminal nucleotide which forms a mismatch with the target sequence. In this instance, primer extension does not occur unless the polymerase used for extension inadvertently possesses exonuclease activity.

The term "genotype" refers to the genetic constitution of an organism. More specifically, the term refers to the identity of alleles present in an individual. "Genotyping" of an individual or a DNA sample refers to identifying the nature, in terms of nucleotide base, of the two alleles possessed by an individual at a known polymorphic site.

The term "polymorphism", as used herein, refers to the coexistence of more than one form of a gene or portion thereof.

The term "PCR", as used herein, refers to the polymerase chain reaction. PCR is a method of amplifying a DNA base sequence using a heat stable polymerase and a pair of primers, one primer complementary to the (+)-strand at one end of the sequence to be amplified and the other primer complementary to the (−) strand at the other end of the sequence to be amplified. Newly synthesized DNA strands can subsequently serve as templates for the same primer sequences and successive rounds of heat denaturation, primer annealing and strand elongation results in rapid and highly specific amplification of the desired sequence. PCR can be used to detect the existence of a defined sequence in a DNA sample.

The term "primer", as used herein, refers to a short single-stranded oligonucleotide capable of hybridizing to a complementary sequence in a DNA sample. A primer serves as an initiation point for template dependent DNA synthesis. Deoxyribonucleotides can be joined to a primer by a DNA polymerase. A "primer pair" or "primer set" refers to a set of primers including a 5' upstream primer that hybridizes with the complement of the 5' end of the DNA sequence to be amplified and a 3' downstream primer that hybridizes with the 3' end of the DNA sequence to be amplified. The term "PCR primer" as used herein refers to a primer used for a PCR reaction. The term "ASPE primer" as used herein refers to a primer used for an ASPE reaction.

The term "tag" as used herein refers to an oligonucleotide sequence that is coupled to an ASPE primer. The sequence is generally unique and non-complementary to the human genome while being substantially complementary to a probe sequence. The probe sequence may be, for example, attached to a solid support. Tags serve to bind the ASPE primers to a probe.

The term "tagged ASPE primer" as used herein refers to an ASPE primer that is coupled to a tag.

The term "anti-tag" or "probe" as used herein refers to an oligonucleotide sequence having a sequence complementary to, and capable of hybridizing to, the tag sequence of an ASPE primer. The "anti-tag" may be coupled to a support.

The term "wild type" as used herein refers to the normal, or non-mutated, or functional form of a gene.

The term "homozygous wild-type" as used herein refers to an individual possessing two copies of the same allele, such allele characterized as being the normal and functional form of a gene.

The term "heterozygous" as used herein refers to an individual possessing two different alleles of the same gene.

The term "homozygous mutant" as used herein refers to an individual possessing two copies of the same allele, such allele characterized as the mutant form of a gene.

The term "mutant" as used herein refers to a mutated, or potentially non-functional form of a gene.

DESCRIPTION OF THE INVENTION

The present invention was developed in response to a need for a rapid, highly specific, and cost-effective method to simultaneously identify multiple genetic risk factors associated with thrombosis. Such identification of risk factors can enhance both treatment and prevention of serious health problems associated with the disease.

The present invention provides a novel, multiplex method of detecting multiple SNPs associated with thrombosis. Specifically, the methodology can be used for the detection of the presence of absence of two or more mutations selected from the group consisting of Factor V Leiden G1691A, Prothrombin (Factor II) G20210A, MTHFR C677T, MTHFR A1298C, factor XIII val34leu, and tissue factor plasma inhibitor (TFPI) C536T. The positive detection of two or more of the mutated forms of each of the above polymorphic sites may be indicative of an individual having a predisposition for thrombosis.

The present invention is further characterized by a high level of specificity. Such specificity is required in order to ensure that any result generated is a true representation of the genomic target and not simply the result of non-specific interactions occurring between reagents present in reactions. This is especially important for multiplexed DNA-based tests where the numerous sequences present in the reaction mixture, most of which are non-complementary, may interact non-specifically depending on the reaction conditions. The ASPE primer and PCR primer sequences described below have been selected due to their minimal cross-reactivity.

The present invention is also characterized by its high level of accuracy when compared to existing methods of detection of SNPs associated with thrombosis, for example, DNA sequencing. Results comparing the two methodologies are provided by example further below.

The methodology of the present invention utilizes the combination of multiplex ASPE technology with hybridization of tagged and labelled extension products to probes in order to facilitate detection. Such methodology is suitable for high-throughput clinical genotyping applications.

In one aspect, the present invention-provides a method for detecting the presence or absence of a variant nucleotide in at least two SNP sites in a sample selected from the group consisting of Factor V Leiden G1691A, Prothrombin (Factor II) G20210A, MTHFR C677T, MTHFR A1298C, Factor XIII G4377T, and tissue factor plasma inhibitor (TFPI) C536T the method comprising the steps of:

Amplifying regions of DNA which may contain the above mentioned variants.

Hybridizing at least two tagged allele specific extension primers to a complementary region of amplified DNA, each tagged allele specific primer having a 3' portion complementary to a region of the amplified DNA, a 3' terminal nucleotide complementary to one allele of one of the mutation sites (wild type or mutant) mentioned above, and a 5' portion complementary to a probe sequence.

Extending tagged ASPE primers, whereby a labelled extension product of the primer is synthesised when the 3' terminal nucleotide of the primer is complementary to a corresponding nucleotide in the target sequence; no extension product is synthesised when the terminal nucleotide of the primer is not complementary to the corresponding nucleotide in the target sequence.

Hybridizing extension products to a probe and detecting labelled extension products. Detection of a labelled extension product is indicative of the presence of the allele complementary to the 3'-terminal nucleotide of the ASPE primer. In the absence of a labelled extension product, it is determined that the allele corresponding to the 3' end of the ASPE primer is not present in the sample.

A general overview of one example of the above-mentioned method is presented in FIG. 1. The present invention should not be limited to the example provided in FIG. 1. A DNA sample is first prepared 10 using methods known in the art. Multiplex PCR amplification 20 is conducted in order amplify regions of DNA containing SNP sites that are associated with thrombosis. A multiplex ASPE reaction 30 is then conducted. By example only, 33 illustrates a wild type and a mutant allele of a gene. At step 36 ASPE primers are hybridized to amplified regions of DNA. If the 3' terminal nucleotide of an ASPE primer is complementary to a corresponding nucleotide in the target sequence, a labelled extension product is formed 39 as will be described further below. The ASPE may be sorted on an addressable universal sorting array 40 wherein the presence of a labelled extension product may be detected using, for example, xMAP detection 50.

DNA Sample Preparation

Patient samples can be extracted with a variety of methods known in the art to provide nucleic acid (most preferably genomic DNA) for use in the following method. In a preferred embodiment, a DNA sample is extracted from whole blood.

Amplification

In a first step at least two regions of DNA containing SNP sites associated with thrombosis are amplified.

In a preferred embodiment of the present invention, PCR amplification of regions containing polymorphic sites associated with thrombosis is initiated using at least two pairs of PCR primers selected from the group of primer pairs consisting of: SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, and SEQ ID NO: 23 and SEQ ID NO: 24. The relationships of each pair of primers to the polymorphic sites mentioned further above is presented in Table 1.

TABLE 1

Primer Pairs Used to Amplify Regions Containing Thrombosis Associated Polymorphic Sites

| Polymorphic Site | Primer Pair |
| --- | --- |
| Factor V Leiden G1691A | SEQ ID NO.: 13 (forward primer) |
| | SEQ ID NO.: 14 (reverse primer) |
| Prothrombin (Factor II) G20210A | SEQ ID NO.: 15 (forward primer) |
| | SEQ ID NO.: 16 (reverse primer) |
| MTHFR C677T | SEQ ID NO.: 17 (forward primer) |
| | SEQ ID NO.: 18 (reverse primer) |
| MTHFR A1298C | SEQ ID NO.: 19 (forward primer) |
| | SEQ ID NO.: 20 (reverse primer) |
| Tissue Factor Plasma Inhibitor (TFPI) C536T | SEQ ID NO.: 21 (forward primer) |
| | SEQ ID NO.: 22 (reverse primer) |
| Factor XIII G4377T | SEQ ID NO.: 23 (forward primer) |
| | SEQ ID NO.: 24 (reverse primer) |

An individual skilled in the art will recognize that alternate PCR primers could be used to amplify the target polymorphic regions, however, in a preferred embodiment the primers listed in Table 1 are selected due to their minimal non-specific interaction with other sequences in the reaction mixture.

ASPE

The ASPE step of the method of the present invention is conducted using at least two tagged ASPE primers selected from the group of ASPE primers consisting of bases 25 and up of SEQ ID NO: 1 to SEQ ID NO: 12.

The ASPE primer set of the present invention has been optimized, as described further below by example, to ensure high specificity and accuracy of diagnostic tests utilizing such allele specific primers.

The ASPE primers of the present invention are as described in table 2.

| Allele Detected | Allele Specific Primer |
| --- | --- |
| Factor V Leiden G1691 | SEQ ID NO: 1 (bases 25 to 46) |
| Factor V Leiden 1691A | SEQ ID NO: 2 (bases 25 to 46) |
| Prothrombin (Factor II) G20210 | SEQ ID NO: 3 (bases 25 to 45) |
| Prothrombin (Factor II) 20210A | SEQ ID NO: 4 (bases 25 to 45) |
| MTHFR C677 | SEQ ID NO: 5 (bases 25 to 44) |
| MTHFR 677T | SEQ ID NO: 6 (bases 25 to 44) |
| MTHFR A1298 | SEQ ID NO: 7 (bases 25 to 46) |
| MTHFR 1298C | SEQ ID NO: 8 (bases 25 to 46) |
| Tissue Factor Plasma Inhibitor (TFPI) C536 | SEQ ID NO: 9 (bases 25 to 43) |
| Tissue Factor Plasma Inhibitor (TFPI) 536T | SEQ ID NO: 10 (bases 25 to 43) |
| Factor XIII G4377 | SEQ ID NO: 11 (bases 25 to 42) |
| Factor XIII 4377T | SEQ ID NO: 12 (bases 25 to 42) |

The 3' end hybridizing portion of the extension primer is hybridized to the amplified material. Where the 3' terminal nucleotide of an ASPE primer is complementary to the polymorphic site, primer extension is carried out using a modified nucleotide. Where the 3' terminal nucleotide of the ASPE primer is not complementary to the polymorphic region, no primer extension occurs.

In one embodiment, labelling of the extension products is accomplished through the incorporation of biotinylated nucleotides into the extension product which may be identified using fluorescent (Streptavidin-Phycoerythrin) or chemiluminescent (Streptavidin-Horseradish Peroxidase) reactions. However, an individual skilled in the art will recognize that other labelling techniques may be utilized. Examples of labels useful for detection include but are not limited to radiolabels, fluorescent labels (e.g fluorescein and rhodamine), nuclear magnetic resonance active labels, positron emitting isotopes detectable by a positron emission tomography ("PET") scanner, and chemiluminescers such as luciferin, and enzymatic markers such as peroxidase or phosphatase.

Each ASPE primer used in the methodology as described above, possess a unique sequence tag at their 5' ends. The sequence tags allow extension products to be detected with a high degree of specificity, for example, through capture on a solid support in order to facilitate detection.

In a preferred embodiment, tags are selected from the group of tags consisting of any one of SEQ ID NO: 1 to SEQ ID NO: 12 (bases 1 to 24).

Detection

The tagged 5' portions of the allele specific primers of the present invention are complementary to probe sequences. Upon hybridization of the allele specific primers to a corresponding probe sequence the presence of extension products can be detected.

In a preferred embodiment, probes used in the methodology of the present invention are coupled to a solid support, for example a 'universal' bead-based microarray.

Examples of supports that can be used in the present invention include, but are not limited to, bead based microarrays and 2D glass microarrays. The preparation, use, and analysis of microarrays are well known to persons skilled in the art. (See, for example, Brennan, T. M. et al. (1995) U.S. Pat. No. 5,474,796; Schena, et al. (1996) Proc. Natl. Acad. Sci. 93:10614-10619; Baldeschweiler et al. (1995), PCT Application WO95/251116; Shalon, D. et al. (1995) PCT application WO95/35505; Heller, R. A. et al. (1997) Proc. Natl. Acad. Sci. 94:2150-2155; and Heller, M. J. et al. (1997) U.S. Pat. No. 5,605,662.). Detection can be achieved through arrays using, for example, chemiluminescence or fluorescence technology for identifying the presence of the SNPs.

Universal arrays function as sorting tools indirectly detecting the target of interest and are designed to be isothermal and minimally cross-hybridizing as a set. Examples of microarrays which can be used in the present invention include, but should not be limited to, Luminex's® bead based microarray systems, and Metrigenix's™ Flow Thru chip technology.

In one embodiment, for example, Luminex's 100 xMAP™ fluorescence based solid support microarray system is utilized. Anti-tag sequences complementary to the tag regions of the ASPE primers/extension products, described above, are coupled to the surface of internally fluorochrome-color-coded microspheres. An array of anti-tag microspheres is produced, each set of microspheres having its own characteristic spectral address. The mixture of tagged, extended biotinylated ASPE primers is combined with the array of anti tagged microspheres and allowed to hybridize under stringent conditions.

In a reaction mixture, a fluorescent reporter molecule (e.g. streptavidin-phycoerythrin) is used to detect labelled extension products which are synthesized when the terminal nucleotide of an ASPE primer is complementary to a corresponding nucleotide in the target sequence.

The reaction mixture, comprising microspheres, extension products etc. is injected into a reading instrument, for example Luminex's 100 xMAP™, which uses microfluidics to align the microspheres in single file. Lasers are used to illuminate the colors both internal to the microspheres, and attached to the surface in the form of extension products hybridized to anti-tag sequences. The Luminex 100 xMAP™, interprets the signal received and identifies the presence of wild type and/or mutant alleles. The presence of the mutant allele of any one or more of the bi-allelic sites consisting of Factor V Leiden G1691A, Prothrombin (Factor II) G20210A, MTHFR C677T, MTHFR A1298C, and tissue factor plasma inhibitor (TFPI) C536T may be indicative of thrombosis, or a pre-disposition to thrombosis. The presence of the mutant allele for factor XIII val34leu has been indicated in providing a weak protective effect against venous thrombosis. Software can be provided which is designed to analyze data associated with the specific extension products and anti-tagged microspheres of the present invention.

In another embodiment, the Metrigenix Flow-Thru three dimensional microchannel biochip (Cheek, B. J., Steel A. B., Torres, M. P., Yu, Y., and Yang H. Anal. Chem. 2001, 73, 5777-5783) is utilized for genotyping as known in the art. In this embodiment, each set of microchannels represents a different universal anti-tag population. Anti-tag sequences corresponding to the tag regions of the ASPE primers/extension products, described above, are attached to the inner surface of multiple microchannels comprising a cell. Multiple cells make up a chip. The reaction mixture, including biotinylated extension products flows through the cells in the presence of a chemiluminescent reporter substrate such as streptavidin-horseradish peroxidase. Microarray chips can be imaged using technology known in the art, such as an ORCA-ER CCD (Hamamatsu Photonics K. K., Hamamatsu City, Japan), and imaging software, in order to identify the genotype of an individual. The presence of the mutant allele of any one or more of the bi-allelic sites consisting of Factor V Leiden G1691A, Prothrombin (Factor II) G20210A, MTHFR C677T, MTHFR A1298C, and tissue factor plasma inhibitor (TFPI) C536T may be indicative of thrombosis, or a pre-disposition to thrombosis. The presence of the mutant allele for factor XIII val34leu has been indicated in providing a weak protective effect against venous thrombosis. Software can be provided which is designed to analyze data associated with the specific extension products and anti-tagged microspheres of the present invention.

An example of the use of the above-mentioned platforms, which also illustrates the specificity and accuracy of the method of the present invention, is provided below.

Kits

In an additional aspect, the present invention provides kits for the multiplex detection of SNPs associated with thrombosis.

A kit according to the present invention may contain the following components including: a PCR primer mix for amplifying regions containing SNP sites of interest optionally including dNTPs), an ASPE primer mix for generation of labelled extension products (optionally including dNTPs) and a solid support, such as microarray beads, the support having anti-tags complementary to the tagged regions of the ASPE primers. In addition, an individual skilled in the art would recognize other components which could be included in such kits including, for example, buffers and polymerases.

Kits of the present invention may include PCR primer pairs, ASPE primers, and tagged supports for all six of the SNP sites or may be customized to best suit the needs of an individual end user. For example, if a customer wishes to detect only three of the SNP sites associated with thrombosis, a kit can be customized to include only the PCR primer pairs, ASPE primers, and support required for the detection of the desired SNP sites. As such, the end user of the product can design a kit to match their requirements. In addition, the end user can also control the tests to be conducted at the software level when using, for example, a universal bead based-microarray for detection. For example, software can be provided with a kit, such software reading only the beads for the desired SNPs or by reporting only the results from the desired SNP data. Similar control of data reporting by software can be obtained when the assay is performed on alternate platforms.

Although the present method has been described in relation to six specific thrombosis associated SNP sites, PCR primers and ASPE primers used to detect additional SNP sites could be included in the above methodology and kits.

All publications, patents and patent applications are herein incorporated by reference in their entirety to the same extent as if each individual publication, patent or patent application was specifically and individually indicated to be incorporated by reference in its entirety The examples presented below are provided to illustrate the present invention and are not meant to limit the scope of the invention as will be apparent to persons skilled in the art.

EXAMPLE #1

ASPE/Microarray Detection of SNPs Associated with Thrombosis

Materials and Methods
1) Oligonucleotides

All oligonucleotides were synthesized by Integrated DNA Technologies (Coralville, Iowa). PCR primers were unmodified and were purified by standard desalting procedures. Universal anti-tags (probes) were 3'-C7 amino-modified for coupling to carboxylated microspheres. All anti-tags were reverse phase HPLC-purified. Chimeric ASPE primers which consisted of a 24mer universal tag sequence 5' to the allele-specific (18-22mer) sequence were also unmodified but were purified by polyacrylamide gel electrophoresis. Following reconstitution, exact oligo concentrations were determined spectrophotometrically using extinction coefficients provided by the supplier. Reconstituted oligos were scanned between 200 and 800 nm and absorbance was measured at 260 nm to calculate oligo concentration.

2) Reagents

Platinum Taq, Platinum Tsp, individual dNTPs and biotin-dCTP were purchased from Invitrogen Corporation (Carlsbad, Calif.). Shrimp alkaline phosphatase and exonuclease I were purchased from USB Corporation (Cleveland, Ohio). Carboxylated fluorescent microspheres were provided by Luminex Corporation (Austin, Tex.). The EDC cross-linker (1-ethyl-3-(3-dimethylaminopropyl) carbodiimide hydrochloride) was purchased from Pierce (Rockford, Ill.). OmniPur reagents including MES (2-(N-morpholino)ethane sulfonic acid), 10% SDS, NaCl, Tris, Triton X-100, Tween-20 and TE buffer were purchased from EM Science (Darmstadt, Germany). The streptavidin-conjugated phycoerythrin was obtained from Molecular Probes Inc. (Eugene, Oreg.).

3) Patient Samples

Genomic DNA from 132 study participants was isolated from whole blood using the Qiagen QIAamp Blood Kit (Qiagen). DNA samples were stored at −20° C. upon isolation. Following shipment, samples were quantified spectrophotometrically by measuring absorbance at 260 nm. Genomic DNA samples were then diluted to 5 ng/uL and stored at 4° C.

4) Genotyping a) MULTIPLEX PCR (6-plex): Multiplex PCR was carried out using 25 ng genomic DNA in a 25 uL final volume. A 'no target' PCR negative control was included with each assay run. The reaction consisted of 30 mmol/L Tris-HCl, pH 8.4, 75 mmol/L KCl, 2 mmol/L MgCl2, 200 umol/L each dNTP, 1.25 units Platinum Taq, with primers ranging from 0.2 to 0.5 umol/L. Samples were cycled in an MJ Research PTC-200 thermocycler (Reno, Nev.) with cycling parameters set at 95° C. for 5 minutes followed by 30 cycles at 95° C. for 30 seconds, 58° C. for 30 seconds and 72° C. for 30 seconds. Samples were then held at 72° C. for 5 minutes and kept at 4° C. until use.

b) ALLELE-SPECIFIC PRIMER EXTENSION: Prior to the ASPE reaction, each PCR reaction was treated with shrimp alkaline phosphatase (SAP) to inactivate any remaining nucleotides (particularly dCTP) so that biotin-dCTP could be efficiently incorporated during the primer extension reaction. Each PCR reaction was also treated with exonuclease I (EXO) to degrade remaining PCR primers in order to avoid any interference with the tagged ASPE primers and the extension reaction itself. To each 25 uL PCR reaction, 2 uL SAP (=2 units) and 0.5 uL EXO (=5 units) were added directly. Samples were then incubated at 37° C. for 30 minutes followed by a 15 minute incubation at 99° C. to inactivate the enzymes. Samples were then added directly to the ASPE reaction.

Multiplex ASPE was carried out using 5 uL of treated PCR product in a final volume of 20 uL. Each reaction consisted of 20 mmol/L Tris-HCl pH 8.4, 50 mmol/L KCl, 1.25 mmol/L MgCl2, 5 umol/L biotin-dCTP, 5 umol/L each of dATP, dGTP and dTTP, 1.5 units Platinum Tsp and 25 nmol/L ASPE primer pool (ie. each ASPE primer present at 500 fmol/reaction). The ASPE reactions were incubated at 96° C. for 2 minutes and then subjected to 40 cycles at 94° C. for 30 seconds, 54° C. for 30 seconds and 74° C. for 60 seconds. Reactions were then held at 4° C. until use.

c) BEAD COUPLING: Amino-modified anti-tag sequences were coupled to carboxylated microspheres following Luminex's one-step carbodiimide coupling procedure. Briefly, 5×10$^6$ microspheres were combined with 1 nmol NH$_2$-oligo in a final volume: of 50 uL 0.1 mol/L MES, pH 4.5. A 10 mg/mL EDC working solution was prepared just prior to use and 2.5 uL was added to the bead mixture and incubated for 30 minutes. A second 2.5 uL aliquot of freshly prepared EDC was added followed by an additional 30 minute incubation. Following washes in 0.02% (v/v) Tween-20 and 0.1% (w/v) SDS, the anti-tag coupled beads were resuspended in 100 uL TE buffer (10 mmol/L Tris, pH 8.0, 1 mmol/L EDTA). Bead concentrations were determined using a Beckman Coulter Z2 Particle Count and Size Analyzer (Coulter Corp, Miami Fla.).

d) UNIVERSAL ARRAY HYBRIDIZATION: Each hybridization reaction was carried out using approximately 2500 beads of each of the twelve anti-tag bearing bead populations. The beads were combined in hybridization buffer (0.22 mol/L NaCl, 0.11 mol/L Tris, pH 8.0 and 0.088% (v/v) Triton X-100) and 45 uL of the mix were added to each well of an MJ Research 96-well plate (Reno, Nev.). A 5 uL aliquot of each ASPE reaction was then added directly to each well. The samples were then heated to 96° C. for 2 minutes in an MJ Research PTC-200 followed by a one hour incubation at 37°

C. Following this incubation, samples were filtered through a 1.2 um Durapore Membrane (Millipore Corp, Bedford, Mass.) and washed once using wash buffer (0.2 mol/L NaCl, 0.1 mol/L Tris, pH 8.0 and 0.08% (v/v) Triton X-100). The beads were then resuspended in 150 uL reporter solution (1 ug/mL streptavidin-conjugated phycoerythrin in wash buffer) and incubated for 15 minutes at room temperature. The reactions were read on the Luminex xMAP. Acquisition parameters were set to measure 100 events per bead population and a 100 uL sample volume. A gate setting was established prior to running the samples and maintained throughout the course of the study.

e) Genotyping by DNA Sequencing

For all samples used in the study, genotyping results obtained using the method of the present invention were compared to genotyping results obtained using dideoxy dye-terminator sequencing chemistry. For each of the 6 SNPs, sequencing was performed in both the forward and reverse directions on PCR amplimers obtained using individual primer pairs.

Data Analysis and Interpretation a) DNA Sequencing: For all 132 patient samples in the study, forward and reverse DNA sequencing data for each of the 6 SNPs within a sample was analyzed. For a sequencing call to be accepted for a particular SNP, a consensus between the two individuals was required. If a consensus was not obtained for a particular SNP, the call was determined to be ambiguous and was eliminated from the study. In addition, if the forward and reverse sequencing data for a particular SNP did not coincide, the call was also determined to be ambiguous and was eliminated from the accuracy study.

b) Genotyping Assay: For each DNA sample tested using the method of the present invention, median fluorescent intensity (MFI) units were collected for each of the 12 bead populations corresponding to each allele within the assay. For each allele, the NET MFI was calculated by subtracting the 'no target' (PCR negative control) MFI values from the MFI values for each allele of a given sample. In order to exclude samples containing insufficient or degraded DNA or samples generating sub-optimal results, acceptance criteria were defined such that, for each allele within the assay, MFI units were required to be at least 10× the 'no target' MFI for that allele AND at least 300. If these criteria were not met, the SNP was not called and was excluded from the accuracy study. For SNPs meeting the data requirements, the genotype was then determined based on the mutant allelic ratio where:

$$\text{Mutant Allelic Ratio} = \frac{(\text{NET } MFI) \text{ mutant allele}}{(\text{NET } MFI) \text{ mutant allele} + (\text{NET } MFI) \text{ wild-type allele}}$$

In other words, the mutant allelic ratio represents the fraction of the total net MFI signal for a given SNP attributed to the presence of the mutant allele. By setting cut-off values, the allelic ratio is used to discriminate homozygous wild-type, homozygous mutant and heterozygous SNP calls. Cut-off values were empirically determined for each individual SNP. Typically, the mutant allelic ratio ranged from 0.00 to 0.10 for homozygous wild-type calls, 0.30 to 0.70 for heterozygous calls and 0.90 to 1.00 for homozygous mutant calls.

Results a) Assay Optimization

The PCR and ASPE components of the genotyping methodology of the present invention were optimized to ensure high specificity, in addition to sufficient yield, when assessed by PCR amplimer intensity and MFI units generated by the Luminex xMAP system.

Figure 2:
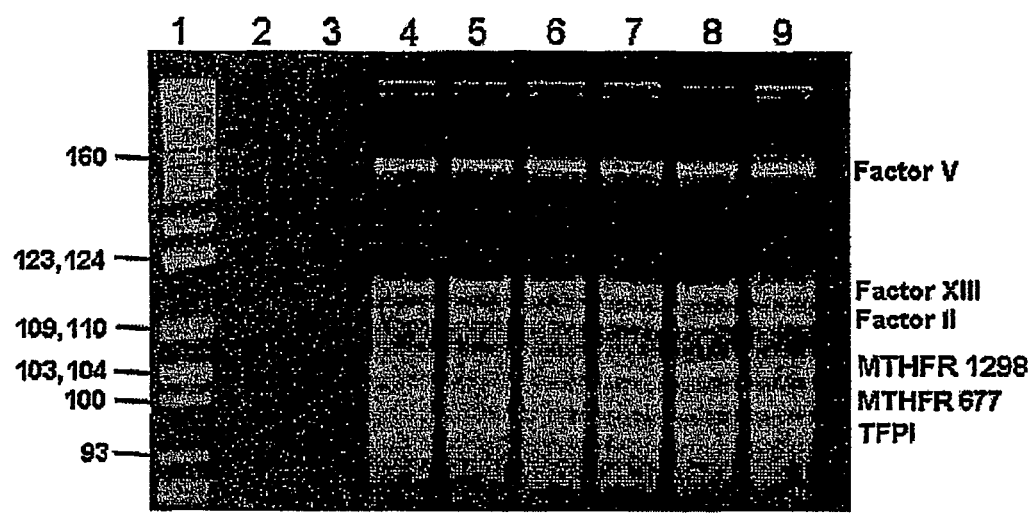
FIG. 2 depicts the high specificity of PCR primers used for multiplex amplification of SNPs associated with thrombosis.

For optimal PCR, buffer composition, cycling parameters, annealing temperature, genomic DNA input as well as primer concentrations for each SNP were examined. PCR products generated under the final optimized conditions were analyzed by gel electrophoresis using the Helixx SuperGel150 system (Scarborough, ON) which is capable of resolving single base-pair differences within products. A gel image of 6 patient samples amplified under optimal conditions is given in FIG. 2 and clearly demonstrates that the multiplex PCR reaction of the present invention was highly specific for the six desired amplimers.

The ASPE component of the method of the present invention was optimized for several parameters affecting specificity and signal output. Parameters examined included cycling parameters, annealing temperature, ASPE primer concentrations and PCR reaction volume added to the ASPE reaction.

Figure 3:
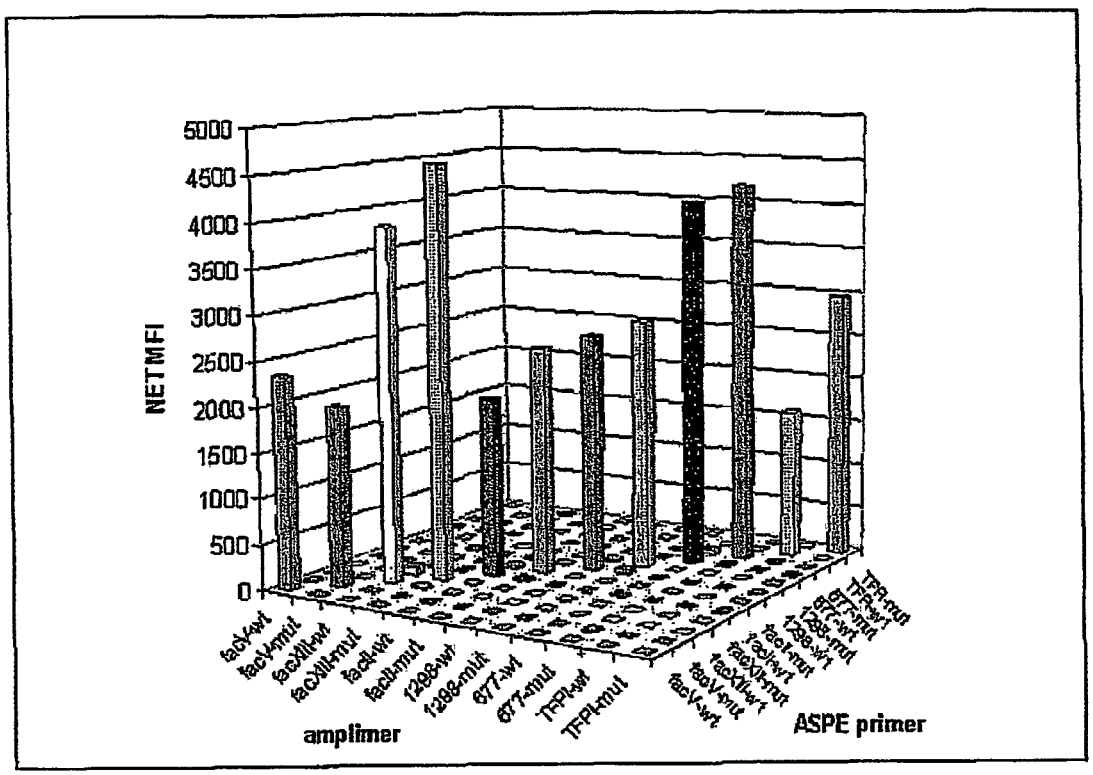
FIG. 3 depicts the high specificity of ASPE primers for specific alleles.

Specificity was for the ASPE reaction where non-specific interactions, detrimental to the end result, may occur between (a) the universal tag sequence and the target alleles and/or (b) the allele-specific primer region and the target alleles. To address this issue of specificity, each allele comprising the thrombophilia panel was PCR-amplified individually and then subjected to ASPE with all twelve universally-tagged ASPE primers present. The ASPE reactions were then sorted on the universal array (ie. all twelve anti-tags present). The signals generated for each individually-amplified allele in the presence of all twelve genotyping primers shown in FIG. 3 clearly indicate that, in the presence of all genotyping primers, each allele reacts only with its corresponding genotyping primer. Two levels of discrimination are built into primer extension genotyping chemistry with one occurring at the hybridization level and the other at the enzymatic extension of a mismatched primer.

From the above experiment, it was also evident that the universal anti-tag sequences hybridize specifically to their complements (tags). Extensive studies on the interactions between the 100 anti-tags from which this subset of twelve was derived have been conducted and the performance of the universal tags has been well-characterized under varying assay conditions. Multiplexed anti-tag mixes using all 100 bead populations were hybridized with each individual complementary tag at various concentrations to check for potential cross-hybridization between universal sequences. Significant cross-hybridization was not observed, with all data clearly supporting the high specificity built into the design of the universal tag sequence set.

b) Patient Study

To assess the clinical accuracy of the method of the present invention, a total of 132 patient DNA samples were genotyped by both the method of the present invention, and DNA dideoxy sequencing for each of the following 6 SNPs: factor V Leiden G1691A, factor II G20210A (prothrombin), MTHFR C677T, MTHFR 1298C, Factor XIII val34leu and TFPI C536T. The DNA samples were selected from consecutive patients with venous thrombosis or age, sex and ethnicity-matched friend controls.

Overall, the method of the present invention was able to generate calls for 779 out of the 792 SNP calls possible for the 132 patient samples analyzed for each of the 6 SNPs. A total of 13 calls resulting from 3 individual samples could not be made due to minimum signal requirements or allelic ratio cut-offs not being met.

The 43 calls not made by sequencing were ambiguous (as defined previously) and were divided among 38 samples. To assess the accuracy within the study, the calls which could not be made either by the method of the present invention or by sequencing were excluded from the calculation. A total of 56 SNPs were eliminated from the study for the purposes of determining accuracy. Of the remaining 736 SNP calls, 14 calls initially showed discordance between the method of the present invention and DNA sequencing. The 14 discordant SNPs were re-sequenced and were found to correspond with the results obtained using the method of the present invention. Thus, following sample re-runs, the method of the present invention showed 100% accuracy for all calls made when compared to sequencing.

Figure 4:
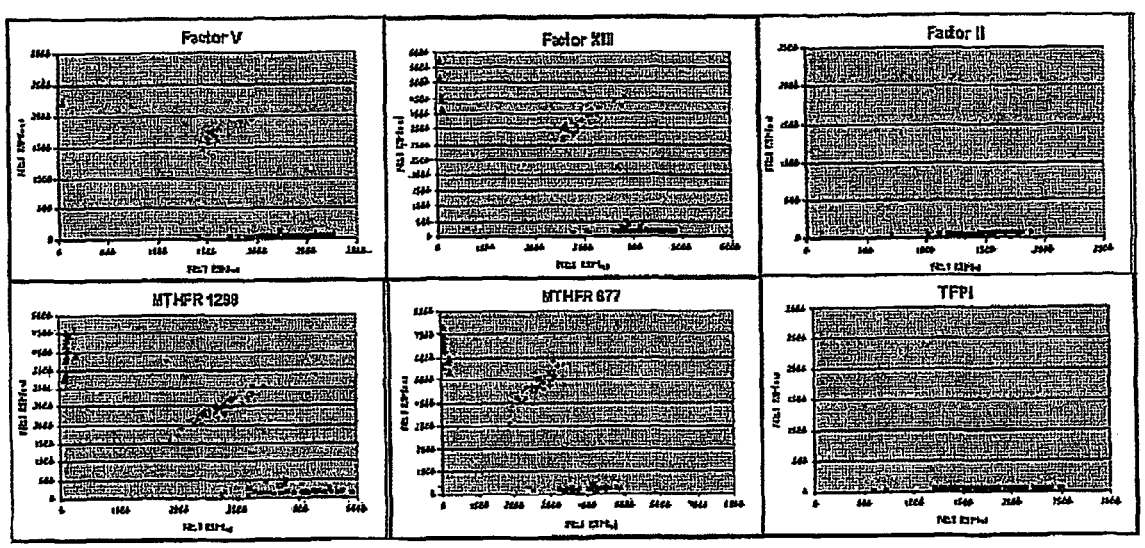
FIG. 4 graphically depicts the ability of the present invention to distinguish between homozygous wild type, heterozygous, and homozygous mutant individuals.

The ability of the method of the present invention to discriminate among the three possible calls (homozygous wild-type, heterozygote and homozygous mutant) is illustrated in FIG. 4. The data clearly demonstrates that each of the call types is tightly clustered within an area that is well-defined and distinct from the other two call types. In other words, overlap between homozygotes and heterozygotes is not likely to occur. This large separation between signals generated for a homozygous wild-type, homozygous mutant or heterozygous sample greatly reduces the risk of miscalls, an extremely important requirement for any diagnostic test. The variation in signal intensities between the different SNPs varies and is likely due to the different priming efficiencies of the ASPE primers and/or the number of incorporated biotin-dCTP nucleotides.

EXAMPLE 2

Multiplex Genotyping of Thrombosis

Figure 5:
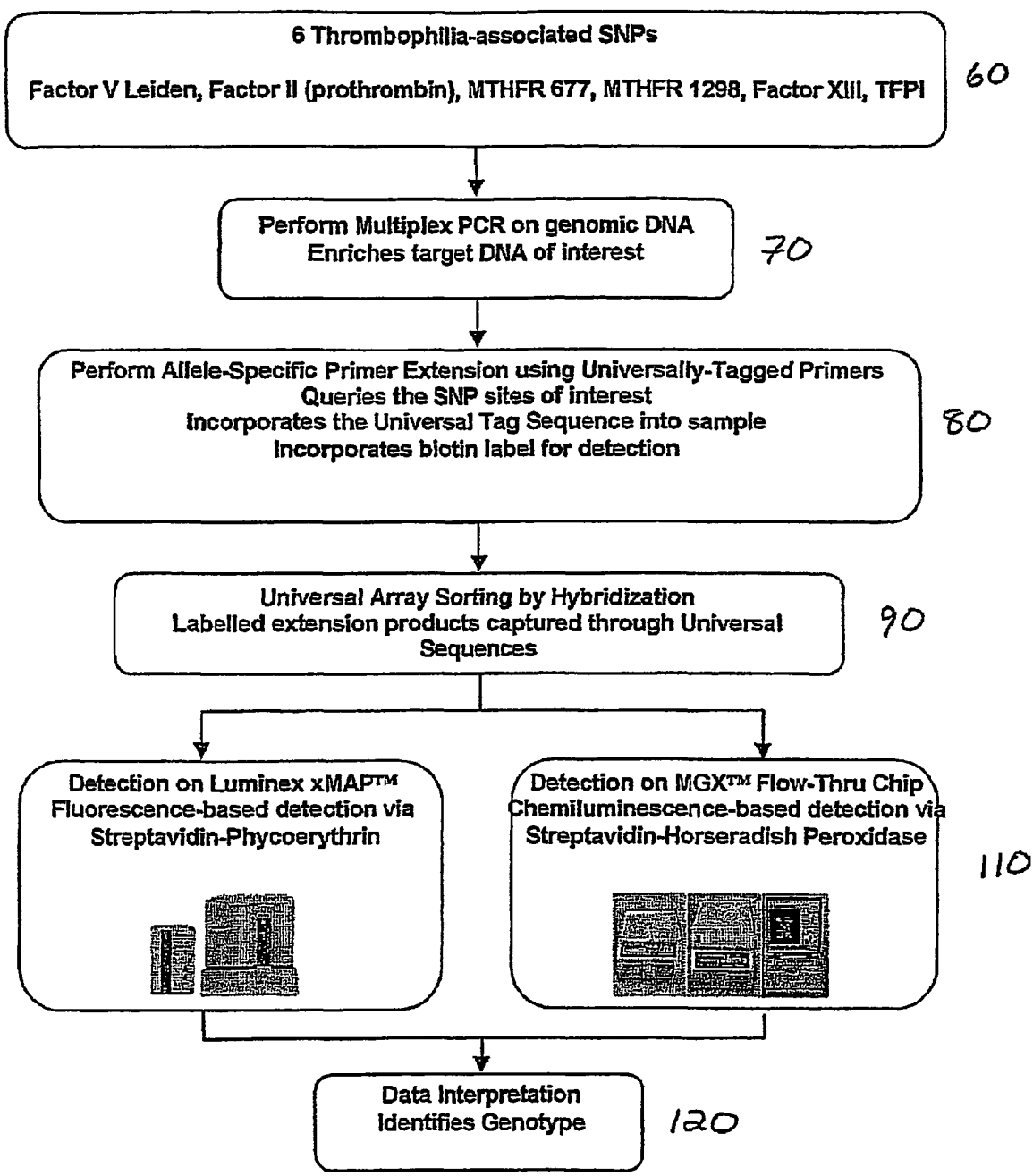
FIG. 5 depicts an overview of methodologies used to detect polymorphisms associated with thrombosis.

FIG. 5 depicts a flow chart overview of a methodology for genotyping of thrombosis using the present invention in conjunction with two distinct detection platforms, specifically the Luminex and Metrigenix microarray platforms. In the method illustrated in FIG. 5, six specific thrombosis-associated SNPs are tested 60. Genomic DNA is subjected to a multiplex amplification reaction 70 to prepare amplified regions of DNA containing the six specific thrombosis-associated SNPs. Tagged ASPE primers are then hybridized to the amplified regions, each tagged allele specific primer having a 3' portion complementary to a region of the amplified DNA, a 3' terminal nucleotide complementary to one allele of one of the mutation sites (wild type or mutant) mentioned above, and a 5' portion complementary to a probe sequence. Extension reactions are initiated, wherein a labelled extension product of the primer is synthesised when the 3' terminal nucleotide of the ASPE primer is complementary to a corresponding nucleotide in the target sequence; no extension product is synthesised when the terminal nucleotide of the primer is not complementary to the corresponding nucleotide in the target sequence. Labelled extension products are then captured on a universal array 90. Detection of extension products can be accomplished either using the Luminex xMAP platform 100, or using an MGX Flow Thru Chip 110. Software is used to interpret the data generated, and to identify the genotype of the individual being tested 120.

All six thrombosis related mutations selected from the group consisting of factor V Leiden G1691A, factor II G20210A (prothrombin), MTHFR C677T, MTHFR A1298C, Factor XIII val34leu and TFPI C536T, were tested for using a combination of the Luminex bead-based array and the Metrigenix Flow-Thru chips. Multiplex PCR amplification of a sample was conducted, as described above, in order to amplify the six polymorphic regions. Allele specific primer extension, as described further above, was also conducted. Extension products were labelled using biotin.

Figure 6:
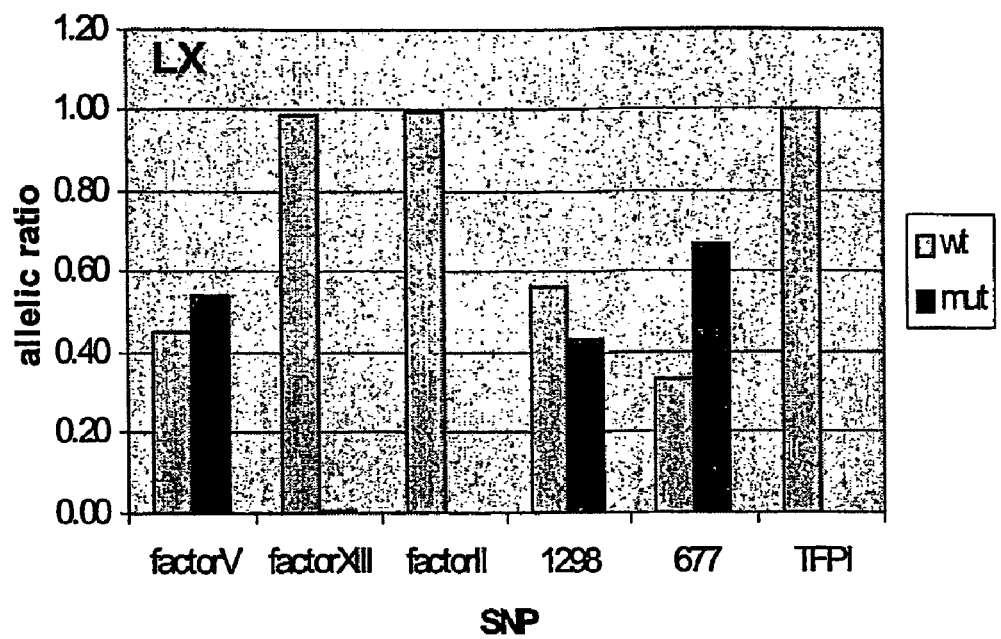
FIG. 6 presents results for genotyping using a Luminex Bead-Based platform.
Figure 7:
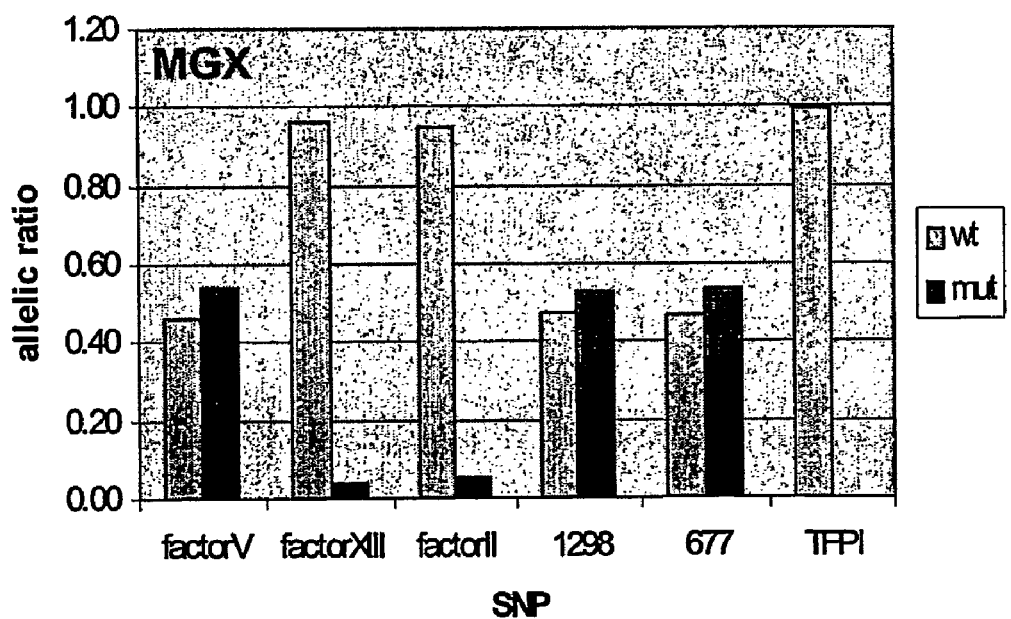
FIG. 7 presents results for genotyping using a Metrigenix Flow-Thru Chip platform.

FIGS. 6 and 7 present the results of a single patient sample genotyped using the universal array format on the Luminex Bead-Based platform (FIG. 6) and the Metrigenix Flow-Thru Chip platform (FIG. 7). Biotinylated extension products in the sample tested were detected through the interaction of the biotin with streptavidin-phycoerythrin when the Luminex bead-based platform was used. Biotinylated extension products in the sample tested were detected through the interaction of the biotin with streptavidin-horseradish peroxidase in the presence of luminal and hydrogen peroxide when the Metrigenix Flow-Thru Chip platform was used.

The results demonstrate the accuracy and specificity of the method of the present invention. All genotypes were correctly identified using both array platforms, and the allelic ratios which were determined using each platform were almost identical.

Although the invention has been described with reference to certain specific embodiments, various modifications thereof will be apparent to those skilled in the art without departing from the spirit and scope of the invention as outlined in the claims appended hereto.

The embodiments of the invention in which an exclusive property or privilege is claimed are defined as follows:

1. A method for detecting in a nucleic acid sample the presence or absence of at least two variant nucleotides associated with thrombosis, the method comprising the steps of:
   a) amplifying from the sample regions of DNA that include at least two selected nucleotide positions for which variants are known to be associated with thrombosis, to form amplified DNA products;
   b) hybridizing at least two tagged allele specific extension primers to a complementary target sequence in the amplified DNA products, wherein each tagged allele specific extension primer has a 3'-end hybridizing portion capable of hybridizing to the corresponding amplified DNA and a 5'-end tag portion complementary to a corresponding anti-tag sequence, the terminal nucleotide of the 3' end hybridizing portion being either complementary to a suspected variant nucleotide or to the corresponding wild type nucleotide, the nucleotide sequences of the at least two tagged allele specific extension primers consisting of sequences selected from the group consisting of SEQ ID NO: 2, SEQ ID NO: 4, SEQ ID NO: 6, SEQ ID NO: 8, SEQ ID NO: 10, and SEQ ID NO: 12;
   c) extending the at least two tagged allele specific extension primers, using labelled nucleotides, if the terminal nucleotide of each 3' end hybridizing portion is a perfect match to the corresponding amplified DNA product; and
   d) hybridizing the at least two tagged allele specific extension primers to their corresponding anti-tag sequences and detecting the presence of labelled extension products.

2. The method of claim 1, wherein the 5'-end tag portions of the at least two tagged allele specific primers each comprise a sequence selected from the group consisting of bases 1 to 24 of SEQ ID NO: 1 to SEQ ID NO: 12 and wherein the sequence of each 5'-end tag portion is different from each other 5'-end tag portion.

3. The method of claim 1 wherein the anti-tag sequence is coupled to a solid support.

4. The method of claim 3 wherein the solid support is selected from the group consisting of beads, spectrally coded beads, and a chip based microarray.

5. The method of claim 1 wherein the step of amplifying is conducted by PCR using a set of PCR amplification primers, said set comprising at least two pairs of PCR primers selected from the group of pairs consisting of:
   SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, and SEQ ID NO: 23 and SEQ ID NO: 24, wherein the at least two pairs of PCR primers are selected for their ability to amplify regions of DNA that include sequences to which the selected at least two tagged allele-specific extension primers will hybridize.

6. A method for detecting in a nucleic acid sample the presence or absence of at least two variant nucleotides associated with thrombosis, the method comprising the steps of;
   a) amplifying from the sample regions of DNA that include at least two selected nucleotide positions for which variants are known to be associated with thrombosis to form amplified DNA products;
   b) hybridizing at least two tagged allele specific extension primers to a complementary target sequence in the amplified DNA products, the nucleotide sequences of the at least two tagged allele specific extension primers consisting of sequences selected from the group consisting of SEQ ID NO: 1 to SEQ ID NO: 12;
   c) extending the at least two tagged allele specific extension primers, using labelled nucleotides, if the terminal nucleotide of each 3' end hybridizing portion is a perfect match to the corresponding amplified DNA product; and
   d) hybridizing the at least two tagged allele specific extension primers to their corresponding anti-tag sequences and detecting the presence of labelled extension products.

7. The method of claim 6 wherein the anti-tag sequence is coupled to a solid support.

8. The method of claim 7 wherein the solid support is selected from the group consisting of beads, spectrally coded beads, and a chip based microarray.

9. The method of claim 6 wherein the step of amplifying is conducted by PCR using a set of PCR amplification primers, said set comprising at least two pairs of PCR primers selected from the group of pairs consisting of:
   SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, and SEQ ID NO: 23 and SEQ ID NO: 24, wherein the at least two pairs of PCR primers are selected for their ability to amplify regions of DNA that include sequences to which the selected at least two tagged allele-specific extension primers will hybridize.

10. An improved method of simultaneously detecting in a sample the presence or absence of variant nucleotides associated with thrombosis, wherein the improvement comprises simultaneously identifying the presence or absence of variant nucleotides associated with thrombosis via allele specific primer extension using a set of primers, the nucleotide sequences of the primers consisting of sequences selected from the group consisting of SEQ ID NO: 2, SEQ ID NO: 4, SEQ ID NO: 6, SEQ ID NO: 8, SEQ ID NO: 10, and SEQ ID NO: 12.

11. An improved method of simultaneously detecting in a sample the presence or absence of variant nucleotides associated with thrombosis, wherein the improvement comprises simultaneously identifying the presence or absence of variant nucleotides associated with thrombosis via allele specific primer extension using a set of primers, the nucleotide sequences of the primers consisting of sequences selected from the group consisting of SEQ ID NO: 1 to SEQ ID NO: 12.

* * * * *

SEQUENCE LISTING

<160> NUMBER OF SEQ ID NOS: 24

<210> SEQ ID NO 1
<211> LENGTH: 46
<212> TYPE: DNA
<213> ORGANISM: Artificial
<220> FEATURE:
<223> OTHER INFORMATION: Tagged ASPE primer
<220> FEATURE:
<221> NAME/KEY: Tag
<222> LOCATION: (1)..(24)

<400> SEQUENCE: 1
tctctttaaa cacattcaac aataggacaa aatacctgta ttcctc                    46

<210> SEQ ID NO 2
<211> LENGTH: 46

-continued

```
<212> TYPE: DNA
<213> ORGANISM: Artificial
<220> FEATURE:
<223> OTHER INFORMATION: Tagged ASPE primer
<220> FEATURE:
<221> NAME/KEY: Tag
<222> LOCATION: (1)..(24)

<400> SEQUENCE: 2
taaatacttc attactaatc acacggacaa aatacctgta ttcctt            46

<210> SEQ ID NO 3
<211> LENGTH: 45
<212> TYPE: DNA
<213> ORGANISM: Artificial
<220> FEATURE:
<223> OTHER INFORMATION: Tagged ASPE primer
<220> FEATURE:
<221> NAME/KEY: Tag
<222> LOCATION: (1)..(24)

<400> SEQUENCE: 3
atctcaatta caataacaca caaacaataa aagtgactct cagcg             45

<210> SEQ ID NO 4
<211> LENGTH: 45
<212> TYPE: DNA
<213> ORGANISM: Artificial
<220> FEATURE:
<223> OTHER INFORMATION: Tagged ASPE primer
<220> FEATURE:
<221> NAME/KEY: Tag
<222> LOCATION: (1)..(24)

<400> SEQUENCE: 4
atactttaca aacaaataac acaccaataa aagtgactct cagca             45

<210> SEQ ID NO 5
<211> LENGTH: 44
<212> TYPE: DNA
<213> ORGANISM: Artificial
<220> FEATURE:
<223> OTHER INFORMATION: Tagged ASPE primer
<220> FEATURE:
<221> NAME/KEY: Tag
<222> LOCATION: (1)..(24)

<400> SEQUENCE: 5
ctttcttaat acattacaac atacgagaag gtgtctgcgg gagc              44

<210> SEQ ID NO 6
<211> LENGTH: 44
<212> TYPE: DNA
<213> ORGANISM: Artificial
<220> FEATURE:
<223> OTHER INFORMATION: Tagged ASPE primer
<220> FEATURE:
<221> NAME/KEY: Tag
<222> LOCATION: (1)..(24)

<400> SEQUENCE: 6
ctaaatcaca tacttaacaa caaagagaag gtgtctgcgg gagt              44

<210> SEQ ID NO 7
<211> LENGTH: 46
<212> TYPE: DNA
<213> ORGANISM: Artificial
<220> FEATURE:
<223> OTHER INFORMATION: Tagged ASPE primer
```

```
<220> FEATURE:
<221> NAME/KEY: Tag
<222> LOCATION: (1)..(24)

<400> SEQUENCE: 7
aatcaacaca caataacatt cataacaaag acttcaaaga cacttt            46

<210> SEQ ID NO 8
<211> LENGTH: 46
<212> TYPE: DNA
<213> ORGANISM: Artificial
<220> FEATURE:
<223> OTHER INFORMATION: Tagged ASPE primer
<220> FEATURE:
<221> NAME/KEY: Tag
<222> LOCATION: (1)..(24)

<400> SEQUENCE: 8
ttaacaactt atacaaacac aaacacaaag acttcaaaga cacttg            46

<210> SEQ ID NO 9
<211> LENGTH: 43
<212> TYPE: DNA
<213> ORGANISM: Artificial
<220> FEATURE:
<223> OTHER INFORMATION: Tagged ASPE primer
<220> FEATURE:
<221> NAME/KEY: Tag
<222> LOCATION: (1)..(24)

<400> SEQUENCE: 9
tcatcacttt ctttactttta cattggctgt atttttttcc agc              43

<210> SEQ ID NO 10
<211> LENGTH: 43
<212> TYPE: DNA
<213> ORGANISM: Artificial
<220> FEATURE:
<223> OTHER INFORMATION: Tagged ASPE primer
<220> FEATURE:
<221> NAME/KEY: Tag
<222> LOCATION: (1)..(24)

<400> SEQUENCE: 10
aactttctct ctctattctt atttggctgt atttttttcc agt               43

<210> SEQ ID NO 11
<211> LENGTH: 42
<212> TYPE: DNA
<213> ORGANISM: Artificial
<220> FEATURE:
<223> OTHER INFORMATION: Tagged ASPE primer
<220> FEATURE:
<221> NAME/KEY: Tag
<222> LOCATION: (1)..(24)

<400> SEQUENCE: 11
atatacttta cactttcaac aaacgacgcc ccggggcacc ac                42

<210> SEQ ID NO 12
<211> LENGTH: 42
<212> TYPE: DNA
<213> ORGANISM: Artificial
<220> FEATURE:
<223> OTHER INFORMATION: Tagged ASPE primer
<220> FEATURE:
<221> NAME/KEY: Tag
<222> LOCATION: (1)..(24)
```

```
<400> SEQUENCE: 12
caataaacat tctttacatt ctcagacgcc ccggggcacc aa                    42

<210> SEQ ID NO 13
<211> LENGTH: 20
<212> TYPE: DNA
<213> ORGANISM: Artificial
<220> FEATURE:
<223> OTHER INFORMATION: Forward primer

<400> SEQUENCE: 13
cgcctctggg ctaataggac                                             20

<210> SEQ ID NO 14
<211> LENGTH: 20
<212> TYPE: DNA
<213> ORGANISM: Artificial
<220> FEATURE:
<223> OTHER INFORMATION: Reverse Primer

<400> SEQUENCE: 14
gccccattat ttagccagga                                             20

<210> SEQ ID NO 15
<211> LENGTH: 20
<212> TYPE: DNA
<213> ORGANISM: Artificial
<220> FEATURE:
<223> OTHER INFORMATION: Foward primer

<400> SEQUENCE: 15
gaaccaatcc cgtgaaagaa                                             20

<210> SEQ ID NO 16
<211> LENGTH: 18
<212> TYPE: DNA
<213> ORGANISM: Artificial
<220> FEATURE:
<223> OTHER INFORMATION: Reverse primer

<400> SEQUENCE: 16
ccagagagct gcccatga                                               18

<210> SEQ ID NO 17
<211> LENGTH: 20
<212> TYPE: DNA
<213> ORGANISM: Artificial
<220> FEATURE:
<223> OTHER INFORMATION: Forward primer

<400> SEQUENCE: 17
ctttgaggct gacctgaagc                                             20

<210> SEQ ID NO 18
<211> LENGTH: 20
<212> TYPE: DNA
<213> ORGANISM: Artificial
<220> FEATURE:
<223> OTHER INFORMATION: Reverse primer

<400> SEQUENCE: 18
caaagcggaa gaatgtgtca                                             20

<210> SEQ ID NO 19
<211> LENGTH: 20
```

```
<212> TYPE: DNA
<213> ORGANISM: Artificial
<220> FEATURE:
<223> OTHER INFORMATION: Forward primer

<400> SEQUENCE: 19
aggagctgct gaagatgtgg                                              20

<210> SEQ ID NO 20
<211> LENGTH: 20
<212> TYPE: DNA
<213> ORGANISM: Artificial
<220> FEATURE:
<223> OTHER INFORMATION: Reverse primer

<400> SEQUENCE: 20
ctttgtgacc attccggttt                                              20

<210> SEQ ID NO 21
<211> LENGTH: 27
<212> TYPE: DNA
<213> ORGANISM: Artificial
<220> FEATURE:
<223> OTHER INFORMATION: Forward primer

<400> SEQUENCE: 21
tctattttaa ttggctgtat tttttc                                       27

<210> SEQ ID NO 22
<211> LENGTH: 20
<212> TYPE: DNA
<213> ORGANISM: Artificial
<220> FEATURE:
<223> OTHER INFORMATION: Reverse Primer

<400> SEQUENCE: 22
tgcggagtca gggagttatt                                              20

<210> SEQ ID NO 23
<211> LENGTH: 20
<212> TYPE: DNA
<213> ORGANISM: Artificial
<220> FEATURE:
<223> OTHER INFORMATION: Forward primer

<400> SEQUENCE: 23
tctaatgcag cggaagatga                                              20

<210> SEQ ID NO 24
<211> LENGTH: 18
<212> TYPE: DNA
<213> ORGANISM: Artificial
<220> FEATURE:
<223> OTHER INFORMATION: Reverse primer

<400> SEQUENCE: 24
tgtgcctgga cccagagt                                                18
```